（12）United States Patent
Han et al.

(10) Patent No.: US 11,504,436 B2
(45) Date of Patent: Nov. 22, 2022

US011504436B2

(54) BIOGENIC HEMIN-BASED MRI CONTRAST AGENTS, AND COMPOSITIONS AND METHODS THEREOF

(71) Applicant: University of Massachusetts, Boston, MA (US)

(72) Inventors: Gang Han, Shrewsbury, MA (US); Yang Zhao, Worcester, MA (US); Jing Peng, Tianjin (CN)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/608,838

(22) PCT Filed: May 17, 2018

(86) PCT No.: PCT/US2018/033074
§ 371 (c)(1),
(2) Date: Oct. 27, 2019

(87) PCT Pub. No.: WO2018/217520
PCT Pub. Date: Nov. 29, 2018

(65) Prior Publication Data
US 2020/0197542 A1 Jun. 25, 2020

Related U.S. Application Data

(60) Provisional application No. 62/509,208, filed on May 22, 2017.

(51) Int. Cl.
*A61K 49/10* (2006.01)

(52) U.S. Cl.
CPC .................. *A61K 49/106* (2013.01)

(58) Field of Classification Search
CPC ..... A61K 49/00; A61K 49/143; A61K 49/106
See application file for complete search history.

(56) References Cited

U.S. PATENT DOCUMENTS 5,817,292 A * 10/1998 Snow .................. A61K 49/128
424/9.323

FOREIGN PATENT DOCUMENTS

| DE | 100 06 570 | * | 8/2001 | |
|---|---|---|---|---|
| DE | 10006570 A1 | | 8/2001 | |
| EP | 3295962 A1 | * | 3/2018 | ........... A61K 49/085 |
| EP | 3295962 A1 | | 3/2018 | |
| WO | WO-98/47539 | * | 10/1998 | |

OTHER PUBLICATIONS

Karel Ulbrich et al, Targeted Drug Delivery with Polymers and Magnetic Nanoparticles:Covalent and Noncovalent Approaches, Release Control, and Clinical Studies, Chem. Rev, 116, 5338-5431. (Year: 2016).*
Ljiljan Fruk et al., Covalent Hemin-DNA Adducts for Generating a Novel Class of Artificial Heme Enzymes, Angew. Chem, int. Ed. 44, 2603-2606. (Year: 2005).*
Inbar Schlachet et al., Protoporphyrin IX-modified chitosan-g-oligo (NiPAAm) polymeric micelles: from physical stabilization to permeability characterization in vitro, Biomaterial Science, (Year: 2016).*
Qingbo Yo et al. Novel core-shell dextran-hemin crosslinked micelles: synthesis, photo-controlled drug release and excellent (synergetic) antitumor effect, J Materials Chem B, 3, 1439. (Year: 2015).*
Jin-Jing Line et al. Crosslinking of hemin to a specific site on the 90-KDa ferritin repressor protein, Proc. Natl. Acad. Sci, 88, 6068-6071. (Year: 1991).*
Sergey P. Martsev at al. Modification of monoclonal and polyclonal IgG with palladium (II) coproporphyrin I: stimulatory and inhibitory functinal effects induced by two different methods, J of Immunological Methods, 186, 293-304. (Year: 1995).*
R. Haselberg et al., Characterization of drug-lysozyme conjugates by sheathless capillary electrophoresis-time-of-flight mass spectrometry, Analytica Chimca Acta, 698, 77-83. (Year: 2011).*
EP18806538.7 Extended European Search Report, dated Feb. 8, 2021.

* cited by examiner

*Primary Examiner* — Michael G. Hartley
*Assistant Examiner* — Jagadishwar R Samala
(74) *Attorney, Agent, or Firm* — Milstein Zhang & Wu LLC

(57) ABSTRACT

The invention provides a novel class of MRI contrast agents based on biogenic hemin and compositions and methods of preparation and use thereof.

1 Claim, 7 Drawing Sheets

BIOGENIC HEMIN-BASED MRI CONTRAST AGENTS, AND COMPOSITIONS AND METHODS THEREOF

PRIORITY CLAIMS AND RELATED APPLICATIONS

This application is the U.S. national phase of and claims priority to PCT/US18/33074, filed May 17, 2018, which claims the benefit of priority from U.S. Provisional Application Ser. No. 62/509,208, filed on May 22, 2017, the entire content of each of which is incorporated herein by reference.

TECHNICAL FIELDS OF THE INVENTION

The invention generally relates to diagnostics and MRI contrast agents. More particularly, the invention relates to a novel class of MRI contrast agents based on biogenic hemin.

BACKGROUND OF THE INVENTION

Magnetic resonance imaging (MRI), a medical imaging technique used in radiology, is one of the most used non-invasive, versatile imaging modalities for clinical detection, staging, and monitoring of the treatment of tumors. MRI affords unique advantages, including high spatial resolution, outstanding soft tissue contrast, and causes no radiation damage. Recently, the development of magnetic contrast agents (CAs) has improved the inherent sensitivity of MRI, enabling this technique to visualize specific biological processes at both cellular and molecular levels. (Sun, et al. 2008 *Adv. Drug Delivery Rev.* 60, (11), 1252-65; Zhang, et al. 2016 *Nanoscale* 8, (20), 10491-510.)

MRI, however, often encounters an inherent low sensitivity since there is little difference between normal and abnormal soft tissues in relaxation time and resulting contrast. To overcome this drawback, materials that possess magnetic properties, namely MRI contrast agents (MRI-CAs), have been used to enhance image quality and signal contrast. It is reported that more than 40% of all MRI examinations utilize a contrast agent. The development of biocompatible and effective MRI-CAs plays an important role in the application of MRI in clinical radiology.

Different magnetic agents have continuously emerged as contrast media for MRI, which are generally classified into two classes. One class is superparamagnetic agents that shorten the T2 relaxation time and produce negative enhancement effects, such as Fe-based CAs such as superparamagnetic iron oxide (SPIO) and ultrasmall superparamagnetic iron oxide (USPIO). The other class is paramagnetic complexes that accelerate the T1 relaxation process and possess positively signal-enhancing ability. Compared with the former, the latter CAs own the merits of signal-brighten effect, concomitant superior signal-to-noise ratio and no susceptibility artefact, thus becoming the most frequently used MRI-CAs in the clinic.

Existing T1 MRI-CAs, however, contain extrinsic metal elements such as gadolinium (Gd) and manganese (Mn), which raise certain biosafety issues. For example, the clinically available Gd-based CAs suffer the shortcomings of short life spans in the body and potential toxicity of free Gd ions that are released from the complex. Meanwhile, intravenous administration of gadolinium-based chelates is reported to induce gadolinium retention in tissues such as the brain, kidney and skin, and potentially lead to serious complications, for example, nephrogenic systemic fibrosis and organ functional failure. Mn-based CAs are extremely toxic to the liver and heart once free Mn ions are released, due to which Mn-based CAs are hardly used for clinical purposes. (Caravan, et al. 1999 *Chem Rev.* 99, (9), 2293-352; Na, et al. 2009 *J. Mater. Chem.* 19, (35), 6267; McDonald, et al. 2015 *J. Radiology* 275, (3), 772-82; Tu, et al. 2012 *Wiley Interdiscip. Rev.: Nanomed. Nanobiotechnol.* 4, (4), 448-57.)

Thus, there is an ongoing need for novel MRI CAs that possess high T1 relaxivity and excellent biosafety.

SUMMARY OF THE INVENTION

The invention provides a novel class of biogenic, non-toxic and effective T1 MRI contrast agents suitable for a wide range of clinical applications. Endogenous hemins derived from blood and conjugates thereof are employed to serve as biogenic and gadolinium-free contrast agents for MR imaging.

The disclosed hemin-based contrast agents can be readily prepared by hydrating hemin in alkaline environment or conjugating hemin with hydrophilic ligands, leading to water-soluble and paramagnetic compounds with remarkable enhancement of T1 effects in in vitro and in vivo MRI. In addition, the hemin-based MRI contrast agents are metabolized and cleared by the living body. The paramagnetic property, favorable toxicity profile and biodegradable ability make this new class of contrast agents promising alternatives to Gd-based CAs in clinical radiology.

In one aspect, the invention generally relates to a method for magnetic resonance imaging (MRI). The method includes administering to a subject in need thereof an aqueous composition comprising $Fe^{3+}$-containing hemin.

In another aspect, the invention generally relates to an aqueous composition suitable for use as an MRI contrast agent. The aqueous composition is comprised of $Fe^{3+}$-containing hemin.

In yet another aspect, the invention generally relates to a contrast agent for MRI that is comprised of $Fe^{3+}$-containing hemin covalently coupled to an oligomer or polymer.

In yet another aspect, the invention generally relates to a method for magnetic resonance imaging. The method includes administering to a subject in need thereof an aqueous composition comprising a $Fe^{3+}$-containing hemin covalently coupled to an oligomer or polymer.

In yet another aspect, the invention generally relates to a method for preparing a polymer conjugated and $Fe^{3+}$-containing hemin. The method includes reacting hematin with an oligo(ethylene oxide) or poly(ethylene oxide) modified with an amino group in the presence of a coupling agent in an aqueous solution.

DETAILED DESCRIPTION OF THE INVENTION

Figure 1:
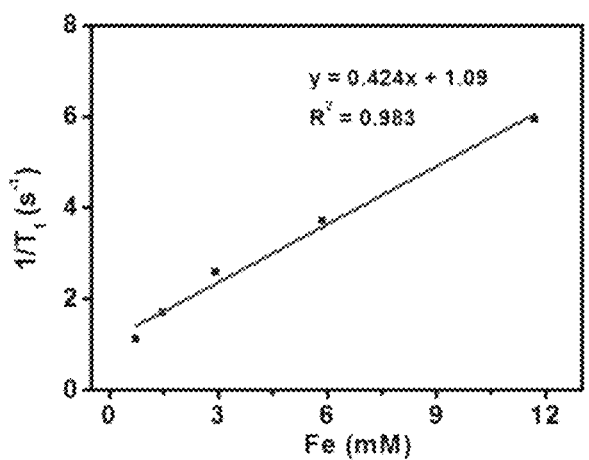
FIG. 1 shows a graph showing r1 values and 1/T1 values according to Fe concentrations of metalloporphyrin-based MRI-CAs after dispersion in water.

The invention is based in part on the unexpected discovery of a novel class of contrast agents based on endogenous and biogenic hemin that are suitable for used in MRI.

MRI contrast agents play an important role in clinic examinations. Gd-based chelates are frequently used. Gd-based CAs suffer from several key shortcomings, including short life spans, insufficient targeting ability, potential toxicity resulting from the release of free Gd ions, and high risk of Gd retention in the kidney, brain and neural tissues. It has long been desired to develop biogenic, nontoxic and efficient T1-MRI contrast agents for clinical applications.

The present invention exploits endogenous hemins derived from blood to afford a novel class of biogenic and gadolinium-free contrast agents for MR imaging. The present invention has demonstrated the paramagnetic property and in vivo biosafety of the hemin-based CAs disclosed herein. For example, a biogenic hemin is shown herein to possess signal-enhancing capability in T1-weighted MRI and is suitable to serve as a contrast agent for MR imaging.

The hemin-based CAs may be prepared, for example, by hydrating hemin in an alkaline environment or by conjugating hemin with hydrophilic ligands. The resulting CAs are water-soluble and paramagnetic and show remarkable enhancement effects in in vitro and in vivo T1 MRI. In addition, the hemin-based MRI contrast agents of the invention are cleared by the living body. Taken together, the superior paramagnetic property, biodegradable ability and favorable toxicity profile make this novel class of CAs a promising alternative to the traditional Gd-based CAs in clinical diagnostic radiology.

Methemoglobin, which is composed of four iron-containing heme groups surrounding a globin group, affect T1 relaxation and display the signal of significant brightness in T1-weighted MRI. This phenomenon is associated with the special space configuration of methemoglobin, in which the iron in the heme group is in the $Fe^{3+}$ (ferric) state, not the $Fe^{2+}$ (ferrous) state of normal hemoglobin.

This form of heme groups containing $Fe^{3+}$ ions, called hemin, is represented as chloro [7,12-diethenyl-3,8,13,17-tetramethyl-21H,23H-porphine-2,18-dipropanoato (2-)-N,N,N,N] iron.

Hemes are most commonly recognized as components of hemoglobin, the red pigment in blood. Chemically, heme is a cofactor consisting of a $Fe^{2+}$ (ferrous) ion contained in the centre of a heterocyclic macrocycle organic compound called porphyrin, which is made up of four pyrrole groups joined together by methine bridges. Not all porphyrins contain iron, but a substantial fraction of porphyrin-containing metalloproteins has heme as the prosthetic group and are known as hemoproteins.

The structural formula for hemin is:

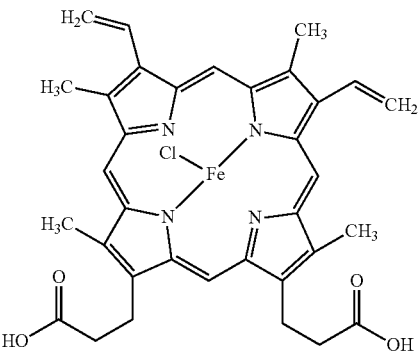

One of the most important biological functions of hemoproteins is electron transfer, where the heme iron and the porphyrin molecule serve as an electron source in redox chemistry and peroxidase reactions, respectively. This ability of electron transfer makes it easy for the $Fe^{2+}$ ion of heme to lose their outer electrons and convert into $Fe^{3+}$ ion with five 3d electrons. The unpaired electrons confer the heme iron with its paramagnetic capacity to shorten T1 relaxation.

Hemin for injection, also known as Panhematin®, is an FDA-approved drug used in the management of porphyria attacks, particularly in acute intermittent porphyria. The term "hematin" has been used to describe the chemical reaction product of hemin and sodium carbonate solution. Hematin is eliminated from the human body by the enterohepatic pathway and the urinary system in the forms of bilirubin metabolites.

Heme, however, exhibits limited dispersibility in aqueous media at physiological pH conditions, which has led to serious challenges in the development of hemin-based contrast-enhancing agents.

In addition, to utilize hemin-based CAs in biomedical imaging, two additional issues are important.

First, hemin is an enzyme inhibitor that limits the synthesis of δ-aminolevulinic acid, which subsequently slow down the rate of the hepatic and/or marrow synthesis of porphyrin. The biosafety of hematin was one of the key factors that restricted its application in vivo, especially for diagnostic purposes. As an enzyme inhibitor, overdose of hemin could inhibit the hepatic and/or marrow synthesis of porphyrin, which may lead to anemia resulting from the limited production of red blood cells. An intravenous infusion of Panhematin® containing a dose of 1 to 4 mg/kg/day of hematin was demonstrated to be safe for clinic applications. An excessive hematin dose (e.g., 12.2 mg/kg) was reported to induce reversible renal shutdown only in a rare case.

Second, further improvement of hematin's T1 relaxivity is desirable, especially for in vivo applications.

The present invention exploits PEGylation of hemin. The results showed that PEGylated hemin possess excellent water solubility and T1 relaxivity. In regard to the aqueous dispersibility, the PEGylated hemin of the invention can be directly dispersed in alkaline solutions at about pH 11. Importantly, when the pH of the alkaline solution containing hemin was reduced back to 7, no changes occurred in the dispersibility of the soluble hemin. In addition, PEGylated hemin also decreased hemin uptake and its biological metabolism in the liver.

Moreover, more hemin molecules can be conjugated within one template, which may enhance their paramagnetic capacity and consequently reduce the required dose. Finally, the size of hemin-containing agents may be regulated below about 6 nm by controlling the PEGylation and the number of the linked heme molecules in order to make the CAs metabolize via the urinary system while providing a sufficient circulation time for MR imaging.

Thus, in one aspect, the invention generally relates to a method for magnetic resonance imaging. The method includes administering to a subject in need thereof an aqueous composition comprising $Fe^{3+}$-containing hemin.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

In certain embodiments, the aqueous composition comprising $Fe^{3+}$-containing hemin is formed, prior to administration, by dispersing hemin in an aqueous solution having a pH in the range from about 5 to about 14 (e.g., from about 5 to about 14, from about 6 to about 14, from about 7 to about 14, from about 8 to about 14, from about 9 to about 14, from about 10 to about 14, from about 11 to about 14, from about 12 to about 14, from about 13 to about 14, from about 5 to about 13, from about 5 to about 12, from about 5 to about 11, from about 5 to about 10, from about 5 to about 9, from about 5 to about 8, from about 5 to about 7, from about 8 to about 12, from about 9 to about 13).

The unit dosage for administration may be adjusted depending on the actual MRI application. In certain embodiments, the unit dosage is from about 0.1 mg/kg to about 1 g/kg (e.g., from about 0.1 mg/kg to about 0.5 g/kg, from about 0.1 mg/kg to about 0.1 g/kg, from about 0.1 mg/kg to about 50 mg/kg, from about 0.1 mg/kg to about 20 mg/kg, from about 0.1 mg/kg to about 10 mg/kg, from about 0.1 mg/kg to about 5 mg/kg, from about 0.1 mg/kg to about 1 mg/kg, from about 1 mg/kg to about 1 g/kg, from about 5 mg/kg to about 1 g/kg, from about 10 mg/kg to about 1 g/kg, from about 50 mg/kg to about 1 g/kg, from about 0.1 g/kg to about 1 g/kg, from about 0.5 g/kg to about 1 g/kg, from about 200 mg/kg to about 800 mg/kg, from about 400 mg/kg to about 800 mg/kg).

The method of MRI may be used to image any suitable organ or tissue of the body of a mammal (e.g., human). Exemplary organs and tissues that may be imaged include the heart, liver, spleen, lung, kidney, brain, eyes, colon, prostate and stomach.

In another aspect, the invention generally relates to an aqueous composition suitable for use as MRI contrast agent. The aqueous composition is comprised of $Fe^{3+}$-containing hemin.

In yet another aspect, the invention generally relates to a contrast agent for MRI. The contrast agent is a $Fe^{3+}$-containing hemin covalently coupled to an oligomer or polymer.

In certain embodiments of the contrast agent, the oligomer or polymer is an oligo(ethylene oxide) or poly(ethylene oxide). In certain embodiments of the contrast agent, the contrast agent is formed by reacting hematin with an oligo(ethylene oxide) or poly(ethylene oxide) modified with an amino group in the presence of a coupling agent.

In certain embodiments of the contrast agent, the oligo(ethylene oxide) or poly(ethylene oxide) has a molecular weight in the range from about 80 to about 8,000,000 (e.g., from about 80 to about 5,000,000, from about 80 to about 2,000,000, from about 80 to about 1,000,000, from about 80 to about 500,000, from about 80 to about 200,000, from about 80 to about 100,000, from about 80 to about 50,000, from about 80 to about 10,000, from about 80 to about 5,000, from about 500 to about 8,000,000, from about 1,000 to about 8,000,000, from about 5,000 to about 8,000,000, from about 10,000 to about 8,000,000, from about 50,000 to about 8,000,000, from about 100,000 to about 8,000,000, from about 500,000 to about 8,000,000, from about 1,000,000 to about 8,000,000, from about 1,000 to about 20,000, from about 20,000 to about 500,000, from about 50,000 to about 200,000).

In certain embodiments of the contrast agent, the oligomer or polymer is selected from chitosan, dendrimers, dextrin, peptides, poly(vinylpyrrolidone-co-dimethyl maleic acid), polysaccharide, polyacrylic acid, hyaluronic acid, liposomes, or protein (e.g., selected from human serum albumin, bovine serum albumin, lysozyme, immunoglobulin, ferritin, antibodies and transferrin).

In yet another aspect, the invention generally relates to a method for magnetic resonance imaging. The method includes administering to a subject in need thereof an aqueous composition comprising a $Fe^{3+}$-containing hemin covalently coupled to an oligomer or polymer.

In certain embodiments of the method, the oligomer or polymer is an oligo(ethylene oxide) or poly(ethylene oxide). In certain embodiments of the method, the contrast agent is formed by reacting hematin with an oligo(ethylene oxide) or poly(ethylene oxide) modified with an amino group in the presence of a coupling agent.

In certain embodiments of the method, the oligo(ethylene oxide) or poly(ethylene oxide) has a molecular weight in the range from about 80 to about 8,000,000 (e.g., from about 80 to about 5,000,000, from about 80 to about 2,000,000, from about 80 to about 1,000,000, from about 80 to about 500,000, from about 80 to about 200,000, from about 80 to about 100,000, from about 80 to about 50,000, from about 80 to about 10,000, from about 80 to about 5,000, from about 500 to about 8,000,000, from about 1,000 to about 8,000,000, from about 5,000 to about 8,000,000, from about 10,000 to about 8,000,000, from about 50,000 to about 8,000,000, from about 100,000 to about 8,000,000, from about 500,000 to about 8,000,000, from about 1,000,000 to about 8,000,000, from about 1,000 to about 20,000, from about 20,000 to about 500,000, from about 50,000 to about 200,000).

In certain embodiments of the method, the oligomer or polymer is selected from chitosan, dendrimers, dextrin, peptides, poly(vinylpyrrolidone-co-dimethyl maleic acid), polysaccharide, polyacrylic acid, hyaluronic acid, liposomes or protein (e.g., selected from human serum albumin, bovine serum albumin, lysozyme, immunoglobulin, ferritin, antibodies, transferrin).

The unit dosage is dependent on the actual MRI application. In certain embodiments, the unit dosage for administration is from about 0.1 mg/kg to about 20 g/kg (e.g., 0.1 mg/kg to about 10 g/kg, 0.1 mg/kg to about 1 g/kg, 0.1 mg/kg to about 500 mg/kg, 0.1 mg/kg to about 100 mg/kg, 0.1 mg/kg to about 20 mg/kg, 0.1 mg/kg to about 5 mg/kg, 0.1 mg/kg to about 1 mg/kg, 1 mg/kg to about 20 g/kg, 10 mg/kg to about 20 g/kg, 100 mg/kg to about 20 g/kg, 500 mg/kg to about 20 g/kg, 1 g/kg to about 20 g/kg, 5 g/kg to about 20 g/kg, 10 mg/kg to about 1 g/kg, 100 mg/kg to about 500 mg/kg).

The method of MRI may be applied to image any suitable organ or tissue, for example, selected from heart, liver, spleen, lung, kidney, brain, eyes, colon, prostate and stomach.

In yet another aspect, the invention generally relates to a method for preparing a polymer conjugated, $Fe^{3+}$-containing hemin. The method includes reacting hematin with an oligo(ethylene oxide) or poly(ethylene oxide) modified with an amino group in the presence of a coupling agent in an aqueous solution.

In certain embodiments, the coupling reaction is conducted in the presence of 1-ethyl-3-(3-dimethylaminopropyl)carbodiimide (EDC) and N-hydroxysuccinimide (NHS). In certain embodiments, the oligo(ethylene oxide) or poly(ethylene oxide) has a molecular weight in the range from about 80 to about 8,000,000 (e.g., from about 80 to about 5,000,000, from about 80 to about 2,000,000, from about 80 to about 1,000,000, from about 80 to about 500,000, from about 80 to about 200,000, from about 80 to about 100,000, from about 80 to about 50,000, from about 80 to about 10,000, from about 80 to about 5,000, from about 500 to about 8,000,000, from about 1,000 to about 8,000,000, from about 5,000 to about 8,000,000, from about 10,000 to about 8,000,000, from about 50,000 to about 8,000,000, from about 100,000 to about 8,000,000, from about 500,000 to about 8,000,000, from about 1,000,000 to about 8,000,000, from about 1,000 to about 20,000, from about 20,000 to about 500,000, from about 50,000 to about 200,000).

The following examples are meant to be illustrative of the practice of the invention and not limiting in any way.

Examples

Hematin was studied for its properties in MR imaging. T1-weighted in vitro imaging was carried out on a 3.0 T MR scanner, demonstrating the concentration-dependent brightening effect of the prepared hematin.

FIG. 1 is a graph showing r1 values and 1/T1 values according to Fe concentrations of metalloporphyrin-based MRI-CAs after dispersion in water. As shown in FIG. 1, the T1 relaxivity value of hematin was measured to be 0.424 $mM^{-1}\ s^{-1}$. To further evaluate its MRI performance in vivo, hematin at a dose of 2 mg/kg/day, which is within the recommended range for clinical use, was administered into the tail veins of nude mice.

Figure 2:
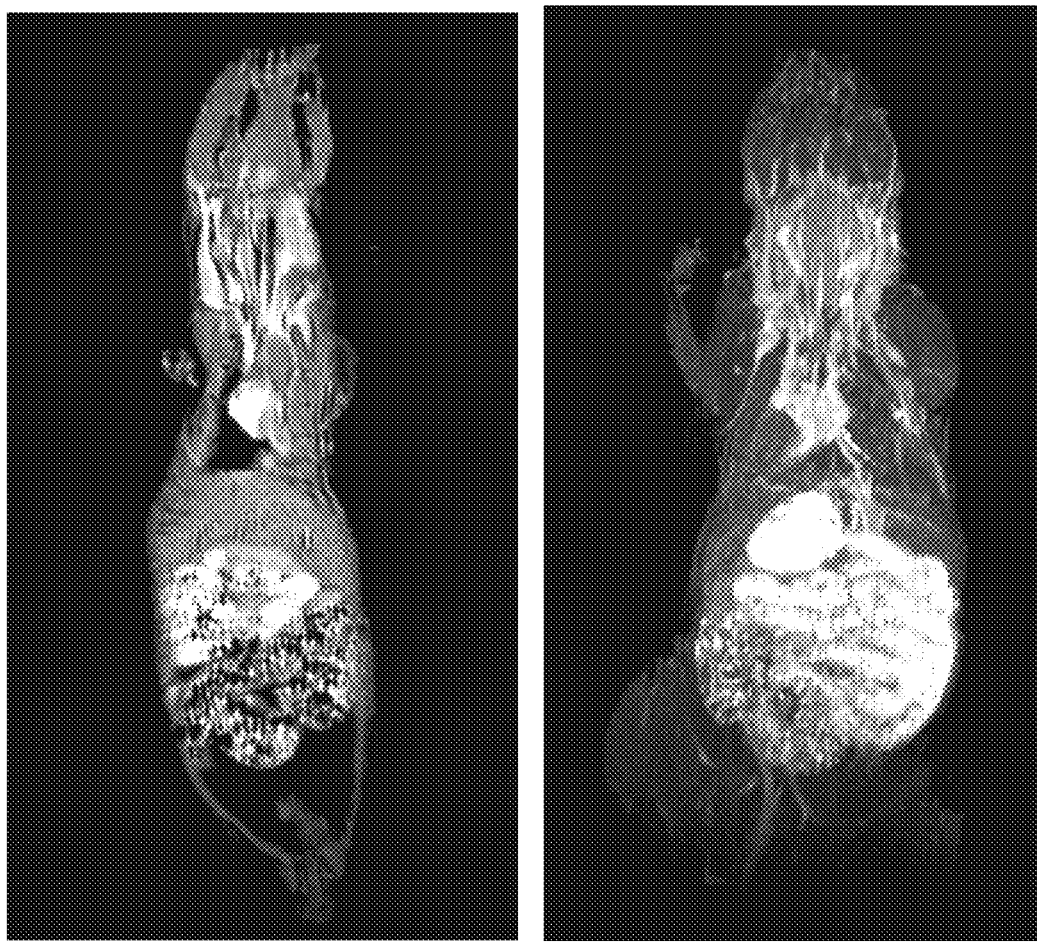
FIG. 2 shows 3D images of MR angiography acquired after intravenous injection to a mouse with metalloporphyrin-based MRI-CAs.

Following intravenous administration, an increase in the T1 signal was clearly observed in the heart and large vessel (FIG. 2), demonstrating the excellent signal enhancement of hematin for MRI. FIG. 2 shows the 3D images of MR angiography acquired from the mouse after intravenous injection with metalloporphyrin-based MRI-CAs.

The biocompatibility of hematin for injection was comprehensively investigated, for example, via blood routine examination, histological analysis, and body weight monitoring.

Table 1 shows the results of blood routine examination acquired from mice intravenous-injected with (Hemin+sodium bicarbonate). All the parameters of blood routine examination at different time points post-injection were within the normal range. Another group of mice injected with PBS were used as control. As shown, almost all the parameters such as WBC, RBC, HGB, PLT, HCT, MCV, MCH, and MCHC, are within the normal range.

TABLE 1

Blood routine examination acquired from mice intravenous-injected with (Hemin + sodium bicarbonate)

|  | Normal Range | Control | 6 h | 12 h | 24 h | 3 d | 5 d | 10 d | 14 d |
| --- | --- | --- | --- | --- | --- | --- | --- | --- | --- |
| WBC (K/μL) | 1.8-10.7 | 2.14 | 4.56 | 4.76 | 2.44 | 6.86 | 3.84 | 3.92 | 4.08 |
| NE (K/μL) | 0.1-2.4 | 0.60 | 0.85 | 0.71 | 0.28 | 0.79 | 0.87 | 0.96 | 0.43 |
| LY (K/μL) | 0.9-9.3 | 1.48 | 2.95 | 3.37 | 1.89 | 5.35 | 2.39 | 2.54 | 3.23 |
| MO (K/μL) | 0.0-0.4 | 0.04 | 0.37 | 0.28 | 0.22 | 0.39 | 0.34 | 0.35 | 0.32 |
| EO (K/μL) | 0.0-0.2 | 0.01 | 0.05 | 0.07 | 0.04 | 0.09 | 0.17 | 0.04 | 0.07 |
| BA (K/μL) | 0.0-0.2 | 0.01 | 0.03 | 0.02 | 0.01 | 0.03 | 0.08 | 0.03 | 0.03 |
| RBC (M/μL) | 6.36-9.42 | 9.22 | 7.29 | 7.82 | 6.31 | 7.73 | 7.20 | 8.72 | 7.14 |
| HGB (g/dL) | 11.0-15.1 | 13.9 | 11.2 | 12.3 | 11.0 | 11.4 | 13.1 | 12.4 | 10.5 |
| HCT (%) | 35.1-45.4 | 46.6 | 35.9 | 40.7 | 43.6 | 37.7 | 41.2 | 45.0 | 44.8 |
| MCV (fL) | 45.4-60.3 | 50.5 | 49.2 | 52.0 | 50.6 | 48.2 | 54.0 | 51.6 | 48.8 |
| MCH (pg) | 14.1-19.3 | 15.1 | 15.4 | 15.7 | 16.2 | 14.6 | 18.1 | 14.2 | 14.7 |
| MCHC (K/μL) | 30.2-34.2 | 29.8 | 31.2 | 30.2 | 32.1 | 30.2 | 31.2 | 30.6 | 30.2 |
| RDW (K/μL) | 12.4-27.0 | 17.5 | 17.2 | 16.0 | 15.3 | 17.9 | 21.7 | 17.4 | 18.4 |
| PLT (K/μL) | 592-2972 | 749 | 643 | 693 | 750 | 963 | 826 | 967 | 617 |
| MPV (fL) | 5.0-20.0 | 5.4 | 5.9 | 6.0 | 6.1 | 5.9 | 6.5 | 5.6 | 5.4 |

White blood cell (WBC), Neutrophils (NE), Lymphocytes (LY), Monocytes (MO), Eosinophils (EO), Basophils (BA), Red blood cell (RBC), Hemoglobin (HGB), Hematocrit (HCT), Mean corpuscular volume (MCV), Mean corpuscular hemoglobin (MCH), Mean corpuscular hemoglobin concentration (MCHC), Red blood cell distribution width (RDW), Platelet Thrombocyte (PLT), Mean platelet volume (MPV).

Figure 3:
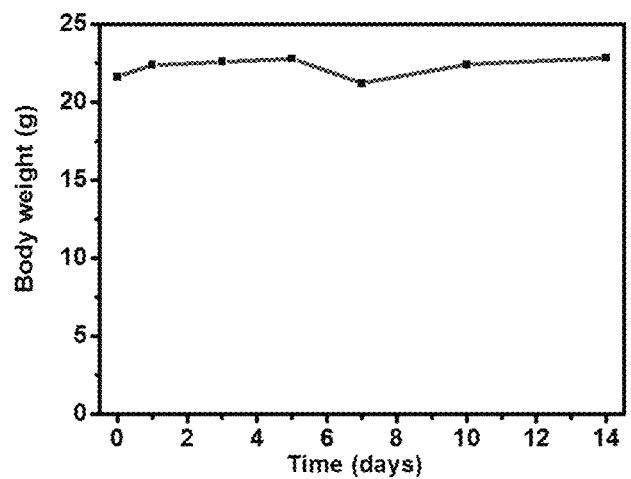
FIG. 3 shows body weight changes of mice according to time after tail vein injection of metalloporphyrin-based MRI-CAs or equal volumes of phosphate-buffered saline (PBS).

FIG. 3 shows body weight changes of mice according to time after tail vein injection of metalloporphyrin-based MRI-CAs or equal volumes of PBS. The histopathological results showed no obvious histological changes in several susceptible organs (e.g., heart, liver, spleen, lung, and kidney) for 14 days after administration. Moreover, the body weight exhibited no significant changes compared to the control group (FIG. 3). The results taken together demonstrate the excellent biocompatibility of hematin for injection in vivo.

Hematin with PEGylation as MRI CAs

A MRI contrast agent was formed by conjugation of hematin with an amphiphilic material (in this case PEG2000) in an organic solvent using coupling agents (1-ethyl-3-(3-dimethylaminopropyl)carbodiimide (EDC) and N-hydroxysuccinimide (NHS)). The formed hydrophilic He-PEG molecules were stable.

In a typical synthesis, 5 mg hematin was dispersed in 2 mL tetrahydrofuran (THF). EDC (5 mg) and NHS (5 mg) were added to the solution to activate the carboxyl groups of hematin. After stirring vigorously for 10 min, 12 mg PEG2000 modified with amino group on the surface, was added to the above mixture. The reaction mixture was kept at 4° C. in the dark for 12 h with continuous stirring. Red precipitation was observed, which indicated the formation of He-PEG crystals. Following the reaction, 2 mL distilled water was poured into the organic solution to make all the precipitation of He-PEG crystals dissolve.

Then, the organic solvent was removed in a rotary evaporator at reduced pressure at 4° C. for 4.0 h. Finally, the resulting He-PEG was purified by centrifugal ultrafiltration with a centrifuge filter tube (Amicon Ultra-15 Centrifugal Filter Unit with Ultracel-30 membrane, 30 KDa, Millipore) at 5,500 rpm for 60 min. Large nanoparticles precipitated and the supernatant containing small He-PEG was decanted, re-dissolved with 2 mL of PBS buffer (pH 7.4, 10 mM) and stored at 4° C. for the following experiments.

Figure 4:
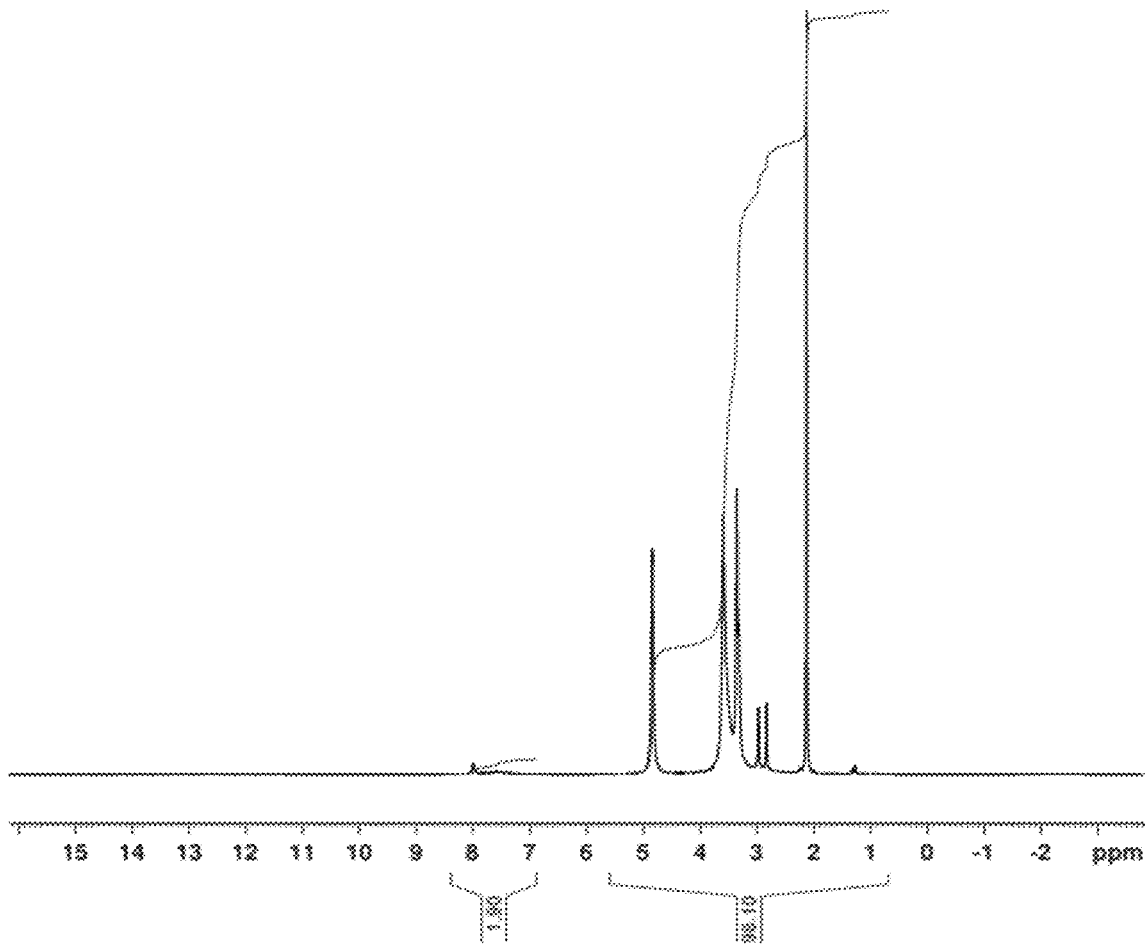
FIG. 4 shows exemplary $^1$H NMR spectra of hydrophilic HeOH—PEG.

The composition of the prepared He-PEG was confirmed by NMR spectroscopy. FIG. 4 shows a $^1$H NMR spectrum of hydrophilic HeOH-PEG according to an embodiment of the present invention. The $^1$H NMR spectrum of the He-PEG nanoparticles confirmed the successful conjugation of He with PEG2000. The magnetic property of the produced He-PEG particles was determined by measuring the longitudinal relaxivity values, which referred to the slope of the 1/T1 (R1) plot versus Fe ion concentration.

Figure 5:
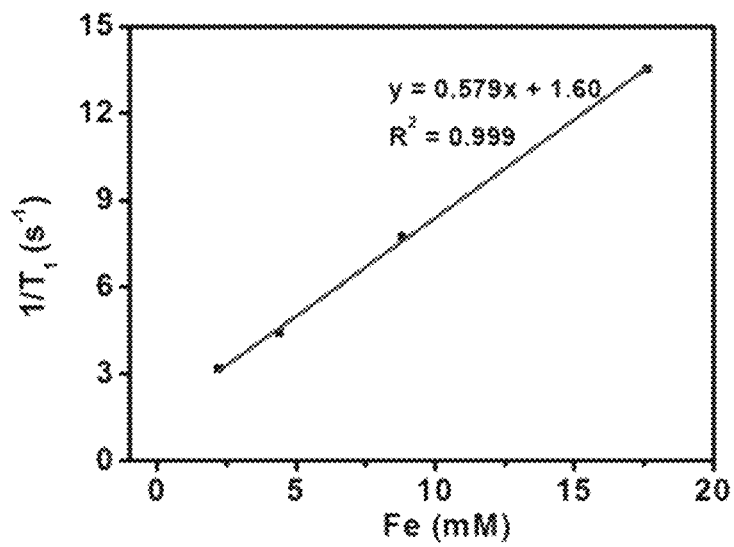
FIG. 5 shows r1 values and 1/T1 values according to Fe concentrations of He—OH after dispersion in water.
Figure 6:
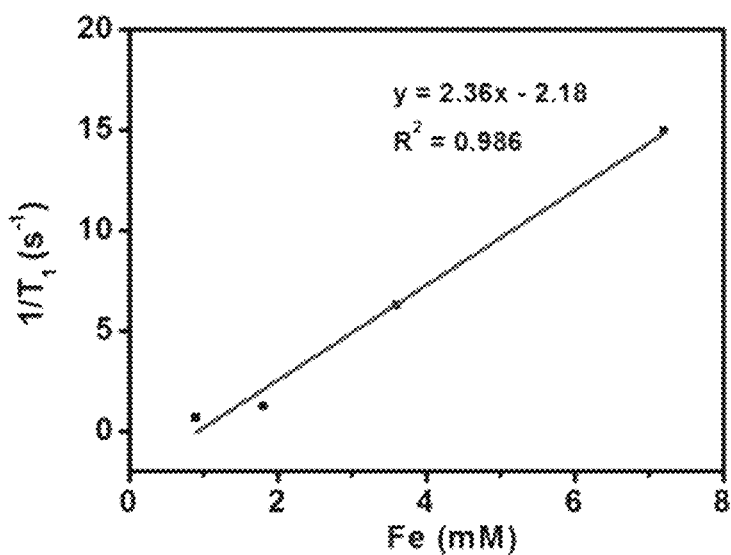
FIG. 6 shows r1 values and 1/T1 values according to Fe concentrations of HeOH-PEG after dispersion in DI water.
Figure 7:
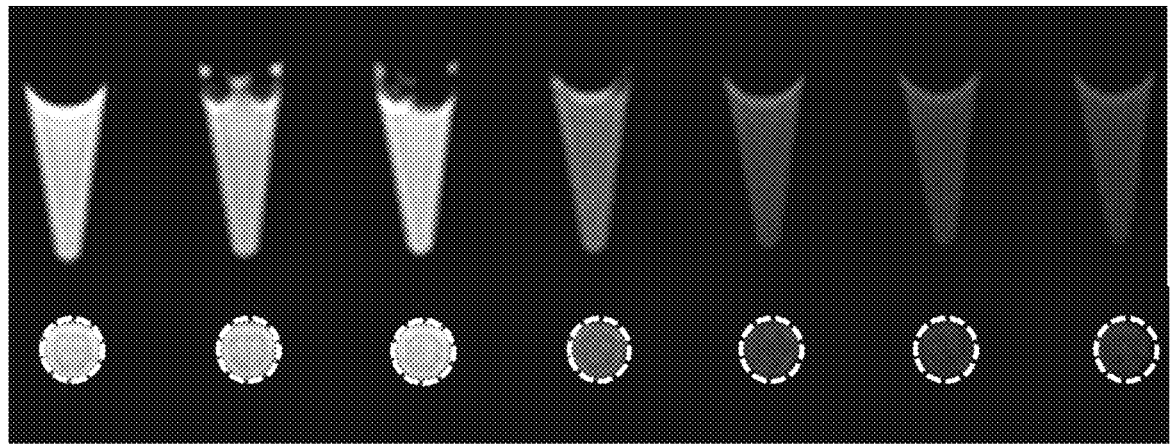
FIG. 7 shows T1-weighted MR images of HeOH-PEG particles according to various Fe concentrations.

FIGS. 5 and 6 show r1 values and 1/T1 values according to Fe concentrations of He—OH after dispersion in water. FIG. 7 shows T1-weighted MR images of HeOH-PEG particles according to various Fe concentrations. The r1 value of the He-PEG particles was found to be 2.36 s$^{-1}$ mM$^{-1}$ Fe (FIG. 5), which was significantly higher than that of He—OH (0.579 s$^{-1}$ mM$^{-1}$ Fe, FIG. 6) and He—CO$_3$ (0.424 s$^{-1}$ mM$^{-1}$ Fe, FIG. 1). Meanwhile, T1-weighted MR images of He-PEG particles with various Fe concentrations are shown in FIG. 7.

HeOH-PEG exhibited strong MR signals at low Fe concentrations. The high r1 values and excellent MR imaging capability showed that the prepared He-PEG particles can serve as a positive MR contrast agent. Importantly, HeOH-PEG exhibited outstanding stability since no visible aggregation or significant change in the longitudinal relaxivity was observed after 3-month storages in deionized (DI) water or phosphate-buffered saline (PBS).

Figure 8:
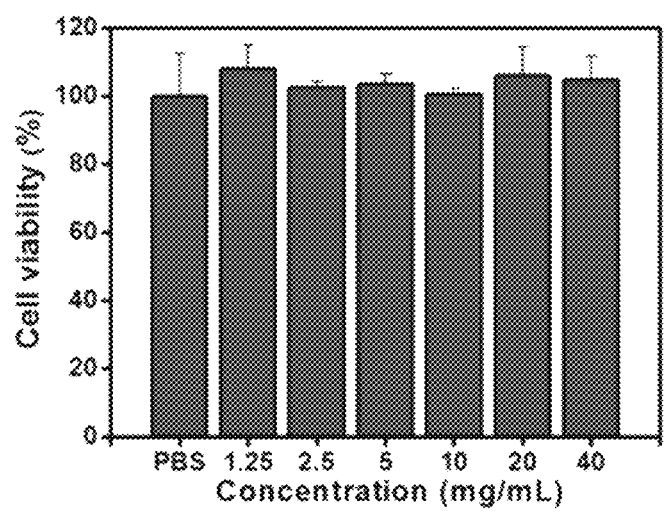
FIG. 8 shows cell toxicities of HeOH-PEG to hela cell.

In vitro and in vivo toxicity profiles of HeOH-PEG were investigated before application of HeOH-PEG in MR imaging of animal models. FIG. 8 shows results of cell toxicity test of HeOH-PEG using HeLa cell. The cytotoxicity of the HeOH-PEG was examined via the MTT assay (3-(4,5-dimethylthiazol-2-yl)-2,5-diphenyltetrazolium bromide). Various concentrations of HeOH-PEG were used to incubate with HeLa cells. Cell viabilities of HeLa cells were not affected by HeOH-PEG when compared to those treated with PBS (FIG. 8), demonstrating the negligible toxicity of HeOH-PEG in vitro.

Figure 9:
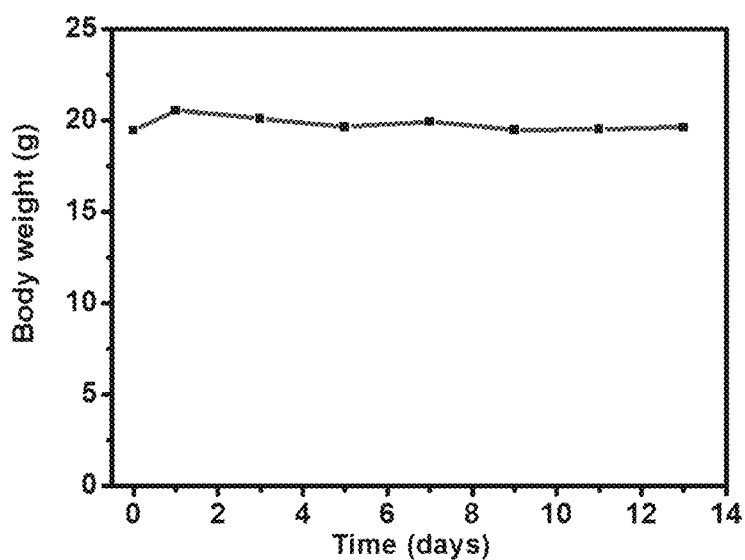
FIG. 9 shows body weight changes of mice according to time after tail vein injection of HeOH-PEG or equal volumes of PBS.

Additionally, HeOH-PEG also exhibited good biocompatibility in vivo. FIG. 9 shows body weight changes of mice according to time after tail vein injection of HeOH-PEG or equal volumes of PBS. After injection of HeOH-PEG, the mice showed no obvious body weight loss during an observational period of 2 weeks.

Meanwhile, blood samples were collected at different intervals after treatment with HeOH-PEG. Table 2 shows the results of blood routine examination acquired from mice intravenous-injected with HeOH-PEG. Another group of mice injected of PBS were used as control. As shown, almost all the parameters such as WBC, RBC, HGB, PLT, HCT, MCV, MCH, and MCHC, were within the normal range. These results confirmed that almost all hematological parameters were within the normal range (Table 2).

Figure 10:
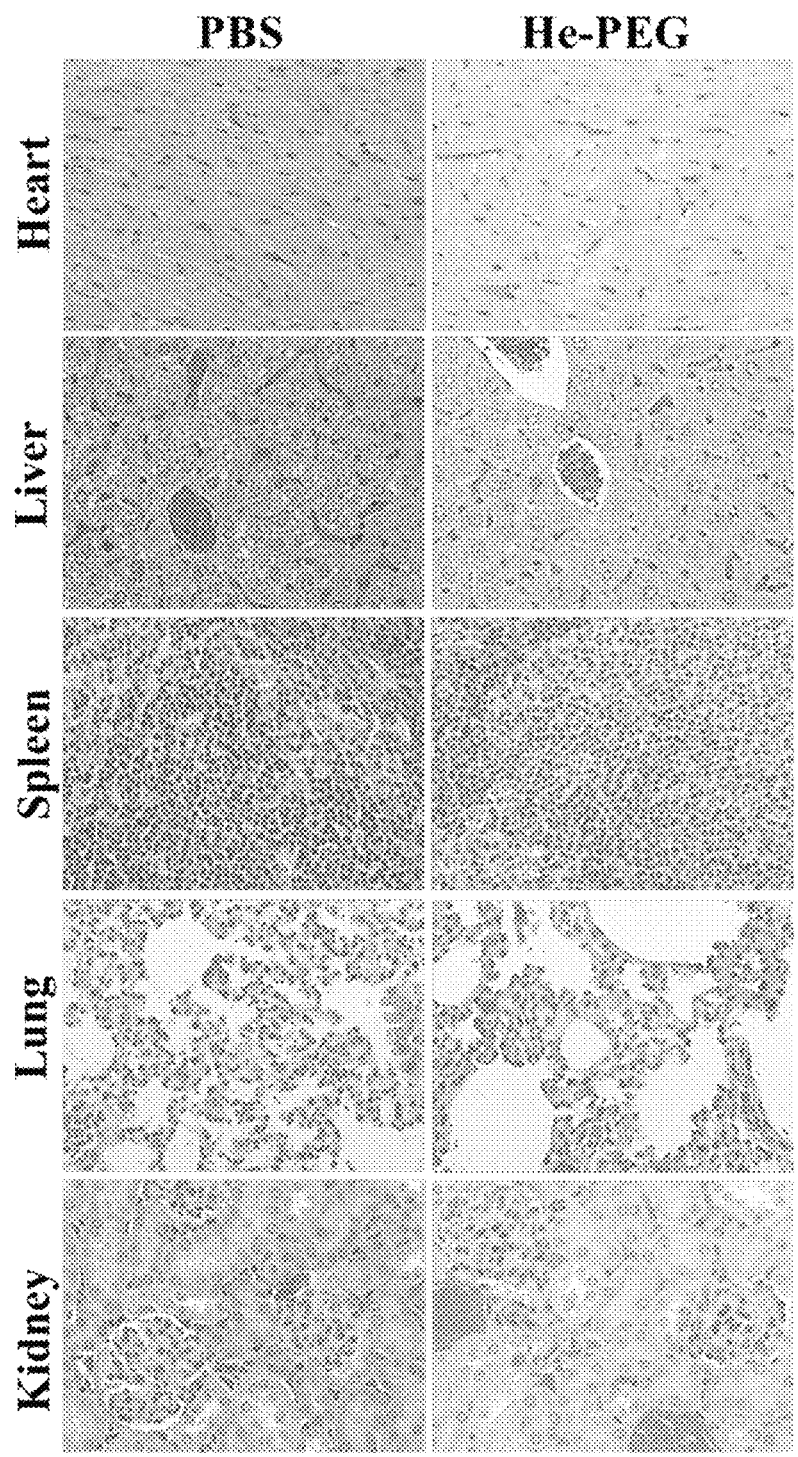
FIG. 10 shows hematoxylin and eosin stained tissue sections of the main visceral organs in mice at 14 day post-injection of metalloporphyrin-based MRI-CAs.

Subsequently, hematoxylin and eosin examinations were performed on major organs (e.g., heart, liver, spleen, lung, and kidney) collected from healthy mice and those treated with HeOH-PEG. The structures of the studied organs appeared normal and showed no tissue damage, inflammation, or necrosis. FIG. 10 shows samples of hematoxylin and eosin stained tissue sections of the main visceral organs in mice at 14 days post-injection of metalloporphyrin-based MRI-CAs. No significant differences were found between the cellular morphology of the studied organs in the HeOH-PEG treated group and the control group (FIG. 10).

These results together demonstrated that HeOH-PEG processed negligible immunogenicity and toxicity.

TABLE 2

Blood routine examination acquired from mice intravenous-injected with HeOH-PEG

| | Normal range | Control | 6 h | 12 h | 24 h | 3 d | 5 d | 10 d | 14 d |
|---|---|---|---|---|---|---|---|---|---|
| WBC (K/µL) | 1.8-10.7 | 4.36 | 5.14 | 4.86 | 4.92 | 5.00 | 3.22 | 3.38 | 3.80 |
| NE (K/µL) | 0.1-2.4 | 0.50 | 1.27 | 1.61 | 1.65 | 2.14 | 0.22 | 1.07 | 0.26 |
| LY (K/µL) | 0.9-9.3 | 3.68 | 3.02 | 2.58 | 3.07 | 2.77 | 2.78 | 1.79 | 2.99 |
| MO (K/µL) | 0.0-0.4 | 0.16 | 0.35 | 0.25 | 0.12 | 0.08 | 0.19 | 0.31 | 0.29 |
| EO (K/µL) | 0.0-0.2 | 0.01 | 0.08 | 0.03 | 0.06 | 0.01 | 0.01 | 0.17 | 0.09 |
| BA (K/µL) | 0.0-0.2 | 0.00 | 0.02 | 0.00 | 0.02 | 0.00 | 0.01 | 0.05 | 0.04 |
| RBC (M/µL) | 6.36-9.42 | 6.38 | 8.02 | 8.86 | 8.94 | 9.64 | 6.29 | 8.24 | 6.88 |
| HGB (g/dL) | 11.0-15.1 | 11.3 | 12.5 | 13.8 | 14.6 | 15.8 | 10.8 | 12.0 | 11.3 |
| HCT (%) | 35.1-45.4 | 41.6 | 41.3 | 46.5 | 45.3 | 46.2 | 44.8 | 45.8 | 35.4 |
| MCV (fL) | 45.4-60.3 | 49.6 | 51.5 | 52.5 | 52.9 | 52.8 | 56.1 | 55.6 | 51.5 |
| MCH (pg) | 14.1-19.3 | 14.6 | 15.6 | 15.6 | 16.3 | 15.8 | 15.8 | 14.6 | 16.4 |
| MCHC (K/µL) | 30.2-34.2 | 29.4 | 30.3 | 29.7 | 30.9 | 29.9 | 28.2 | 30.2 | 31.9 |
| RDW (K/µL) | 12.4-27.0 | 17.0 | 16.5 | 16.1 | 16.7 | 17.1 | 22.2 | 18.2 | 18.6 |
| PLT (K/µL) | 592-2972 | 593 | 890 | 671 | 632 | 570 | 700 | 683 | 751 |
| MPV (fL) | 5.0-20.0 | 5.6 | 5.9 | 5.5 | 6.0 | 6.3 | 5.9 | 6.7 | 5.7 |

Figure 11:
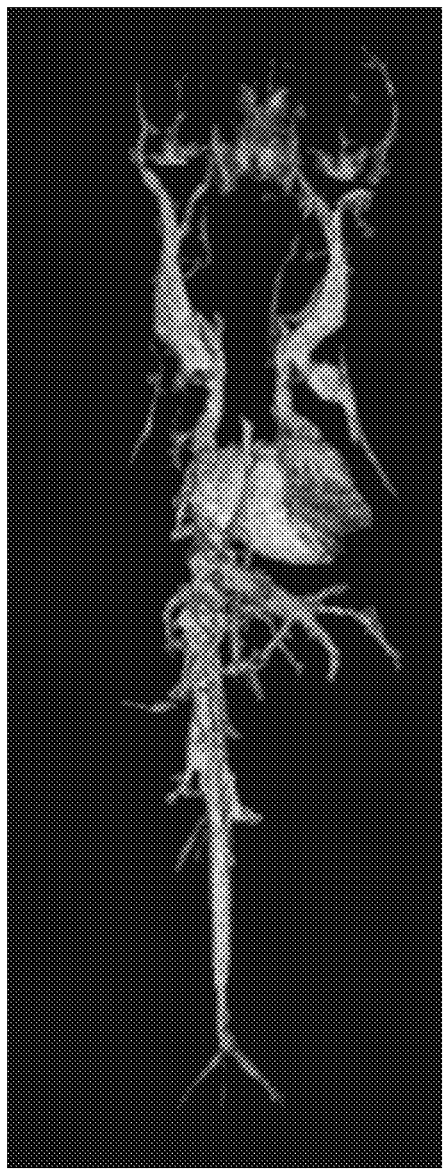
FIG. 11 shows a 3D image of MR angiography acquired from a mouse after intravenous injection with HeOH-PEG.

To study the potential application of HeOH-PEG for in vivo MRI, a series of MR imaging were performed at different time points after HeOH-PEG was injected via tail vein into health node mice (500 µL, 0.48 mmol Au per kg mice). FIG. 11 is the 3D image of MR angiography acquired from the mouse after intravenous injection with HeOH-PEG.

As shown in FIG. 11, MR signal in the great vessels of the mice became stronger as early as 5 min post-injection by comparison with the initial MR images prior to injection. At 20 min post injection, the HeOH-PEG particles flowed through the vessels in liver and kidney, making the kidney contour and the liver brighten. The MR signal enhancement with excellent contrast in the vasculature lasted until 60 min post injection. Then, the vascular MR signal gradually decreased and most of the HeOH-PEG particles were mainly accumulated in kidney, resulting in renal MR signal enhancement. At 2 h post injection, the bladder exhibited remarkable hyperintensity, indicating that the HeOH-PEG particles were excreted from the body by the urinary system. After 24 h post injection, the probe was mostly cleared from the body as the MR signal of the whole body returned back to the baseline level. The in vivo MRI results showed that HeOH-PEG can indeed act as an efficient and clearable contrast agent for MR imaging.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:
1. A method for magnetic resonance imaging (MRI), comprising administering to a subject in need thereof an aqueous composition comprising $Fe^{3+}$-containing hemin covalently coupled to lysozyme as a contrast agent.

* * * * *